United States Patent [19]
Ginger et al.

[11] 3,980,772
[45] Sept. 14, 1976

[54] METHODS OF DISSOLVING BLOOD CLOTS AND THE LIKE WITH STREPTOKINASE CHEMICALLY BONDED TO A CARBOHYDRATE MATRIX

[75] Inventors: Leonard George Ginger, Glenview; Adaline Nicoles Mather, Evanston, both of Ill.

[73] Assignee: Baxter Laboratories, Inc., Deerfield, Ill.

[22] Filed: Sept. 30, 1971

[21] Appl. No.: 185,423

Related U.S. Application Data

[62] Division of Ser. No. 881,632, Dec. 2, 1969, Pat. No. 3,638,213.

[52] U.S. Cl. ................................ 424/94; 424/180
[51] Int. Cl.$^2$ ........................................ A61K 37/48
[58] Field of Search ................ 424/94; 195/DIG. 11

[56] References Cited
UNITED STATES PATENTS 3,226,304   12/1965   Siiteri et al. ..................... 424/94

FOREIGN PATENTS OR APPLICATIONS 1,815,332   7/1969   Germany .......................... 424/94

OTHER PUBLICATIONS

Steinbuch et al., *Bibliotheca haematologica*, No. 19, pp. 169–173, 1962.

Axen et al., Nature, vol. 214, pp. 1302–1304, June 1967.

*Primary Examiner*—Sam Rosen
*Attorney, Agent, or Firm*—W. Garrettson Ellis; Louis Altman

[57] ABSTRACT

One part by weight of streptokinase is chemically bonded to one to five hundred parts by weight of a carbohydrate, to form a material which has improved stability compared with free streptokinase.

6 Claims, No Drawings

METHODS OF DISSOLVING BLOOD CLOTS AND THE LIKE WITH STREPTOKINASE CHEMICALLY BONDED TO A CARBOHYDRATE MATRIX

The application is a division of application Ser. No. 881,632, filed Dec. 2, 1969 now U.S. Pat. No. 3,638,213.

BACKGROUND OF THE INVENTION

Streptokinase is effective to dissolve various types of blood clots both within and outside of the body. However, a number of difficulties are encountered in the use of the enzyme in therapeutic treatment. Antibodies against streptokinase are present in the blood of essentially all human beings but the antibody level or "titer" varies widely among individuals. In order for treatment with streptokinase to be effective, the blood of each patient must be titrated to determine the proper initial dose of enzyme sufficient to nullify the antibodies present in the blood and to provide the proper level of streptokinase enzyme to function as desired, while avoiding the deleterious effects of an excessive dose of streptokinase.

Further, during treatment, the patient develops an increased concentration of antibodies to the enzyme. Hence, a subsequent treatment with streptokinase at a later date may require an increased streptokinase dosage. Also, a subsequent dose may be dangerous since the patient can become "sensitized" to the enzyme, and may thus undergo a severe allergic reaction.

Additionally, doses of the enzyme must be adequate in the first place in order to effectively dissolve blood clots, and they must be administered repeatedly or continuously, generally by intravenous drip, since the enzyme is metabolized by the body in a relatively short period of time.

Accordingly, there is a need for a substrate having a streptokinase-like activity, yet which has increased stability in the body and which also is less subject to neutralization by the antibodies present in the blood stream to make possible a reduction in the amount and frequency of the dosage. Along with such reduced dosages, the danger of allergic reaction and other side effects is reduced.

DESCRIPTION OF THE INVENTION

The composition of this application comprises one part by weight of streptokinase, chemically bonded to from one to five hundred parts by weight of a carbohydrate support medium. This material exhibts a streptokinase-like clot dissolving activity, yet it has improved stability in the blood stream, and is less subject to inactivation by blood antibodies than is free streptokinase. Because of this fact, it becomes frequently unnecessary to titrate the individual patient's blood, so that a standardized dose can be more easily utilized to achieve the dissolution of blood clots, emboli and the like.

Preferably, streptokinase is covalently bonded to the carbohydrate support medium with from ten to two hundred parts of the support medium being present for each part by weight of streptokinase. It is also preferred for the carbohydrate support medium used to be water dispersible or water soluble so that the chemically bonded product is able to form colloidal solutions having a particle size of less than about 2 microns. Such colloidal solutions of streptokinase chemically bonded to a carbohydrate can be directly injected, and can circulate freely in the blood without causing serious side effects due to blockage of capillaries and small blood vessels. In this manner, the chemically bonded streptokinase is brought into contact with the clot to act on it.

Streptokinase is produced by many strains of hemolytic streptococci, including those of Group A and Lancefield Group C streptococci. The selected streptococci can be conventionally cultured, and the crude streptokinase isolated in a conventional manner. Pyrogenic materials can be removed from the streptokinase preparation, for example, by utilizing the teachings of the Mather et al. U.S. Pat. No. 3,255,094.

The support media used herein may constitute carbohydrates such as cellulose, dextran, starch, dextrins, or other polysaccharides, preferably having a molecular weight of about 70,000 to about 500,000. Carbohydrate derivatives are also included in the term "carbohydrate", including alkali metal containing derivatives, caerbohydrate-containing polymers such as copolymers of sucrose and epichlorohydrin, carbohydrates etherified with aminoalkyl groups such as aminoethyl, and carboxyl-containing derivatives such as carboxyethylcellulose, carboxymethyldextran, and other carboxyalkylcarbohydrates such as carboxypropyldextran and the like. Typically, the carbohydrate support media are chemically modified to provide bonding sites for the streptokinase enzyme.

A carbohydrate support medium having pending carboxylic acid groups, such as the carboxyalkylcarbohydrates, can be converted to an azide in the manner typified in Example I below. The azide is then reacted directly with streptokinase, generally at a low temperature between about 0 and 10°C., to yield a covalently bonded adduct of streptokinase and the carbohydrate support medium of the formula

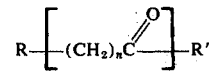

in which R is the carbohydrate support medium having a bond on an oxygen atom thereof connected to the moiety within the brackets, R' is said streptokinase having a bond connected to the moiety, typically on an amino nitrogen or a sulfhydryl sulfur atom of the streptokinase, referring to the condition of the atom of the streptokinase prio to reaction with the moiety, and $n$ is a positive integer, preferably 1 or 2.

Another technique for producing a chemical bond between a carbohydrate support medium having pendant carboxylic acid groups and streptokinase is to add a diorganocabodiimide to a mixture of the support medium and streptokinase in the manner exemplified by Examples 4, 5 and 6, to yield a product in which carbonyl groups of the support medium's carboxylic acid groups are directly bonded to the streptokinase, typically to amine nitrogen atoms thereof.

Carbohydrate support media can be covalently bonded to streptokinase as illustrated in Example 3 by the use of a triazine of the formula

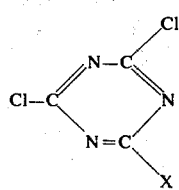

to covalently bond streptokinase to a carbohydrate through a moiety of the formula shown within the brackets

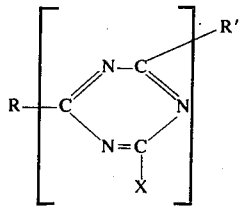

to which R and R' are as defined above, and X is a halogen, hydrogen, or monovalent hydrocarbon radical or no more than about four carbon atoms. When X is a halogen, it also can be replaced with R or R' group.

Likewise, carbohydrate support media can be chemically bonded to streptokinase by means of cyanogen bromide as shown in Example 6. The activation reaction is generally run under alkaline conditions, e.g. a pH of at least 7.5 and preferably above 11.

The compositions of this invention can be used to dissolve blood clots and the like by direct administration of a colloidal solution to the clot site, or by passing blood, plasma, or the like through a bed of an insoluble composition of this invention. In this latter circumstance, it is generally preferred to use larger particle sizes, generally in the visible range. An extracorporial circuit can be arranged by loosely packing a particulate composition of this invention into a cartridge, in which blood plasma, whole blood, or another solution passes through tubing into one end of the cartridge, through the particulate composition of this invention, and out of the particulate composition, generally past a filter and through an exit tubing. If desired, the blood or other fluid can be directly withdrawn from a subject and/or then administered to the subject after treatment.

Similarly, conventional reaction columns containing the material of this invention can be used, or the material of this invention can be impregnated in a matrix such as silicone rubber and incorporated in tubing through which the material to be treated passes.

The following examples are offered for illustrative purposes only, and are not intended to limit the scope of the invention.

EXAMPLE 1

Ten grams of the sodium salt of carboxymethyl dextran having a weight average molecular weight of about 100,000, 15 ml. of concentrated hydrochloric acid, and 250 ml. of methanol are heated at reflux for four hours. The solvent is removed by vacuum distillation, and the residue suspended in 50 ml. of methanol. A 20% solution of hydrazine in methanol is added and stirred until no more white precipitate is formed. The precipitate is then stirred for four hours, filtered and dried. 5 grams of the precipitated product are then resuspended in 150 ml. of 2% hydrochloric acid, and cooled to between 0° and 5° C. An excess of dilute nitrous acid solution is added slowly with constant stirring.

The resulting product is precipitated and washed with methanol. The precipitate consists largely of dextran having

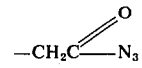

units linked to oxygen atoms of the dextran, the material being informally called dextran azide.

After careful washing, the dextran azide is redissolved in a water solution of about 0.05 to 0.1 M disodium phosphate and 0.9 weight percent sodium chloride, adjusted to about pH 7.0. The concentration of dextran azide is adjusted to about 25 to 50 mg. per ml. of the phosphate-saline buffered solution.

Purified streptokinase is then dissolved in the above solution at a level of about 100,000 enzyme units per ml. of solution, and allowed to stand for about 12 hours (the enzyme units being as defined by the National Institutes of Health).

The resulting mixture is then passed through a "molecular sieve" comprising a material such as the crosslinked dextran sold under the name Sephadex 150 or Sephadex 200, or the commercially available material Biogel P, which is a crosslinked polyacrylamide.

The resulting filtrate is a solution containing dextran which is covalently bonded to streptokinase by a linkage or moiety shown within the brackets of the formula

in which R is dextran, bonded to the linkage through an oxygen atom of the dextran, and R' is the streptokinase connected to the linkage. It is believed that the major portion of the linkages to the streptokinase are connected thereto through amine nitrogen atoms of the streptokinase. The free streptokinase is absorbed by the "molecular sieve", and can be removed by further washing.

The resulting product exhibits the capability of dissolving blood clots and the like, while also showing growing greater stability at ambient and warm temperatures when compared with free streptokinase.

Alternatively, free streptokinase can be separated from the covalently bonded dextran-streptokinase composition by precipitation of the free streptokinase with ammonium sulfate, and then removing of the precipitate by filtering or centrifuging. Excess salt and other ionic materials can be removed from the dextran-streptokinase solution by dialysis or in any other conventional manner.

EXAMPLE 2

Equivalent results are obtained when the experiment of Example 1 is repeated using carboxyethyldextran having a weight average molecular weight of about 300,000 in substitution for the sodium salt of carboxymethyldextran.

Furthermore, after the dextran azide is prepared from the above and filtered, good results are obtained by dissolving the dextran azide prepared above to saturation in a 0.05 M solution of tris(hydroxymethyl)aminomethane buffer having a pH of approximately 8.0 with the purified streptokinase being then placed into the solution and allowed to stand with stirring for about 16 hours.

EXAMPLE 3

A. Dextran having a molecular weight of about 200,000 is dissolved in a saturated solution of sodium bicarbonate. Cyanuric chloride is added in such a concentration as to provide about one mole of cyanuric chloride for each mole of —ONa group present upon the dextran. The mixture is then stirred for about one hour at room temperature, filtered to remove any insoluble material, and dialyzed against saturated sodium bicarbonate to remove any unreacted cyanuric chloride.

Purified streptokinase is added to provide about 100,000 enzyme units (as defined above) per ml. of solution containing the dissolved cyanuric chloride-dextran reaction product, and the mixture is allowed to react for about 14 hours at 5° C. Any remaining free streptokinase is separated from the resulting covalently bonded dextran-streptokinase by passing the material through a "molecular sieve" or by precipitation of the free streptokinase with ammonium sulfate.

The resulting material exhibits blood clot dissolving activity, and has increased stability with respect to free streptokinase.

B. Generally equivalent results to the above are obtained when the dextran is replaced with a sucrose-containing polymer (Ficoll, a copolymer of sucrose and epichlorohydrin, manufactured by Pharmacia of Uppsala, Sweden) having a weight average molecular weight of 400,000, or when cyanuric chloride is replaced with any of compounds A through G below, each of the formula

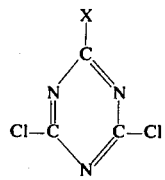

in which X represents the respective radicals shown below:

| Compound | A | bromide |
|---|---|---|
|  | B | methyl |
|  | C | hydrogen |
|  | D | imopropyl |
|  | E | n-butyl |
|  | F | iodide |
|  | G | allyl |

EXAMPLE 4

Approximately 30 to 50 mg. of carboxymethyl cellulose are weighed into a 25 ml. Erlenmeyer Flask. Dilute hydrochloric acid is added in a dropwise manner to adjust the pH between four and five. From three to five mg. of dicyclohexylcarbodiimide, and 0.2 to 0.5 mole of tetrahydrofuran (as solubilizing agent) are added, and the mixture is stirred for twelve to sixteen hours, the pH being kept from falling below 4 by periodic addition of sodium bicarbonate.

The resulting product is filtered and washed with water. The product is resuspended in 2 ml. of 0.10 M potassium phosphate buffer, pH 6.5, and to this is added 2 ml. of 0.5 molar aqueous sodium chloride containing 2 mg. of purified streptokinase. The product contains cellulose which is bonded to streptokinase by a linkage shown within the brackets of the formula

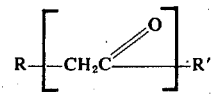

in which R is cellulose bonded to the linkage through a free oxygen atom of the cellulose, and R' is streptokinase bonded to the linkage. It is believed that the major portion of the linkages to the streptokinase are connected thereto through amine nitrogen atoms of the streptokinase. The product shows clot decomposing activity.

Equivalent results to the above are obtained when carboxymethyl-cellulose is replaced with a carboxymethylated copolymer of sucrose and epichlorohydrin having a weight average molecular weight of about 400,000.

EXAMPLE 5

Generally equivalent results to those obtained in Example 4 are obtained upon substitution of dicyclohexylcarbodiimide by either 1-cyclohexyl-3-(2-morpholinyl)-4-ethylcarbodiimide methyl-p-toluene-sulfonate or 4-morpholinodimethylaminopropylcarbodiimide, in the absence of tetrahydrofuran.

EXAMPLE 6

When any of the following carbodiimides are substituted for the carbodiimide used in Example 4, adding tetrahydrofuran or another solubilizing agent as necessary, generally equivalent results to those of Example 4 are obtained:
carbodiimide
dimethylcarbodiimide
diethylcarbodiimide
diisopropylcarbodiimide
di-sec-butylcarbodiimide
diphenylcarbodiimide
dibenzylcarbodiimide
dioctylcarbodiimide
1-ethoxyethyl-3-aminoethylcarbodiimide

EXAMPLE 7

Two grams of cyanogen bromide are dissolved in 50 ml. of distilled water adjusted to a pH of 11.5 by addition of aqueous sodium hydroxide solution. Two grams of dextran having a weight average molecular weight of 500,000 are added, and the suspension is magnetically stirred for approximately 30 minutes. The dextran is precipitated by addition of 50% ethyl alcohol, centrifuged, and washed with absolute ethanol. Excess ethanol is removed under vacuum.

Five hundred mg. of the resulting material, the structure of which is uncertain at the present time are dissolved in 5 ml. of 0.10 M sodium phosphate buffer, pH 7.5, and 5 mg. of streptokinase are added. The mixture is stirred for sixteen hours while the temperature is maintained at 4° C.

The resulting mixture comprises dextran chemically bonded to streptokinase, and has streptokinase-like clot dissolving activity.

Equivalent results are obtained upon substituting a commercially availble copolymer of sucrose and epichlorohydrin for dextran in this experiment.

What is claimed is:

1. The process of dissolving blood clots and the like present in a living subject which comprises bringing into contact with said clot a composition of matter which comprises one part by weight of streptokinase chemically bonded to from ten to 200 parts by weight of a water soluble dextran support medium, said composition of matter being in the form of a colloidal solution having a particle size of less than 2 microns.

2. The process of claim 1 in which said composition of matter is directly injected to said living subject.

3. The process of claim 2 in which said composition of matter is prepared by contacting a carbohydrate with cyanogen bromide under alkaline conditions to form a reaction product therebetween, and thereafter contacting one part by weight of streptokinase with from 10 to 200 parts by weight of said reaction product to form a chemically bonded adduct.

4. The process of claim 3 in which said alkaline conditions used for preparing said reaction product constitute an aqueous medium having a pH of at least 11 in which said dextran and cyanogen bromide are placed.

5. The process of claim 3 in which said dextran has a molecular weight of about 70,000 to about 500,000.

6. The process of claim 5 in which said dextran has a molecular weight of about 70,000.

* * * * *